United States Patent
Ebesu et al.

(10) Patent No.: US 6,652,807 B1
(45) Date of Patent: Nov. 25, 2003

(54) CIGUA-DART METHOD FOR DETECTION OF CIGUATERA TOXINS

(75) Inventors: Joanne S. M. Ebesu, Waipahu, HI (US); Paul Pernambuco-Wise, Honolulu, HI (US)

(73) Assignee: Oceanit Test Systems, Inc., Honolulu, HI (US)

( * ) Notice: Subject to any disclaimer, the term of this patent is extended or adjusted under 35 U.S.C. 154(b) by 0 days.

(21) Appl. No.: 09/901,016

(22) Filed: Jul. 10, 2001

Related U.S. Application Data
(60) Provisional application No. 60/218,048, filed on Jul. 13, 2000.

(51) Int. Cl.[7] .............................................. G01N 21/00
(52) U.S. Cl. ..................... 422/58; 422/100; 422/101; 422/102; 422/104; 435/808; 435/283.1; 435/288.7; 436/165; 436/175; 600/562; 600/566
(58) Field of Search .................. 422/58, 100, 101, 422/102, 103, 104; 435/808, 283.1, 287.2, 288.7; 436/165, 166, 174, 175, 177, 180; 600/562, 564–567

(56) References Cited

U.S. PATENT DOCUMENTS

| | | | |
|---|---|---|---|
| 4,816,392 A | | 3/1989 | Hokama |
| 5,238,652 A | | 8/1993 | Sun et al. |
| 5,266,497 A | | 11/1993 | Imai et al. |
| 5,525,525 A | | 6/1996 | Hokama |
| 5,611,999 A | * | 3/1997 | Dosmann et al. ......... 422/82.05 |
| 5,866,430 A | | 2/1999 | Grow |
| 5,869,003 A | * | 2/1999 | Nason et al. .................. 422/58 |
| 5,919,356 A | * | 7/1999 | Hood et al. ..................... 210/85 |
| 5,935,864 A | * | 8/1999 | Schramm et al. ............ 436/174 |
| 5,939,021 A | * | 8/1999 | Hansen et al. ................. 422/55 |
| 6,004,820 A | * | 12/1999 | Brayton et al. .............. 436/165 |
| 6,040,191 A | * | 3/2000 | Grow et al. ................. 436/174 |

OTHER PUBLICATIONS

Hokama et al.; *A radio immunoassay for the detection of ciguatoxin*; Toxicon, vol. 15 (1977); pp. 317–325.

Tachibana, Kazuo; *Structural Studies of Marine Toxins*; Ph.D. Dissertation in Chemistry, Univ. of Hawaii, Aug. 1980.

Kimura et al.; *Comparison of three different assays for the assessment ciguatoxin in fish tissues: radioimmunoassay, mouse bioassay, and in vitro guinea pig atrium assay*; Toxicon, vol. 20, No. 5, (1982); pp. 907–912.

Hokama, Y.; *A rapid smplified enzyme immunoassay stick test for the detection of ciguatoxin and related polyethers from fish tissues*; Toxicon, vol. 23, No. 6, (1985); pp. 939–946.

Lewis, Nancy D.; *Epidemiology and Impact of Ciguatera in the Pacific; A Review*; Marine Fisheries Review, vol. 48, No. 4, (1986); pp. 6–13.

(List continued on next page.)

Primary Examiner—Christopher L. Chin
Assistant Examiner—Gary W. Counts
(74) Attorney, Agent, or Firm—James Creighton Way; Mara P. Narasimhan

(57) ABSTRACT

A device for rapidly collecting tissue samples from organisms serves as a reaction chamber. It includes a solvent used to extract the analyte, a filter, and optional bioconcentrators. The filtered suspension is irradiated with a predetermined wavelength and the emitted, scattered, or reflected photons transmitted to a detector that identifies and quantifies the analyte. The bioconcentrators may consist of antibodies and colloidal metal nanoparticles that enhance emission of Raman signal frequencies by analytes bound to the antibodies. Alternatively, the device may contain only the extraction solvent and a filter.

20 Claims, 2 Drawing Sheets

OTHER PUBLICATIONS

Lombet et al.; *Ciguatoxin and brevetoxins share a common receptor site on the neuronal voltage–dependent Na+ channel*; Federation of European Biochemical Societies Letters, vol. 219, No. 2, (Jul. 1987); pp. 355–359.

Taylor et al.; *Optimization of a Flow Injection Sampling System for Quantitative Analysis of Dilute Aqueous Solutions Using Combined Resonance and Surface–Enhanced Raman Spectroscopy (SERRS)*; Applied Spectroscopy, vol. 44, No. 4, (1990); pp. 635–640.

Hokama, Y.; *Simplified Solid–Phase Immunobed Assay for Detection of Ciguatoxin and Related Polyethers*; Journal of Clinical Laboratory Analysis, vol. 4, (1990); pp. 213–217.

Kang Xi et al.; *Deteermination of Low Concentrations of the Azo–Dye Complex of Nitrite in Fresh Water and Seawater Using Surface–Enhanced Resonance Raman Spectroscopy (SERR)*; Applied Spectroscopy, vol. 46, No. 5, (1992); pp. 819–826.

Yasumoto et al.; *Marine Toxins*; Chemical Review, vol. 93, (1993); pp. 1897–1909.

Hokama et al.; *Evaluation of the Hawaiian Reef Fishes with the Solid Phase Immunobead Assay*; Journal of Clinical Laboratory Analysis, vol. 7, (1993); pp. 26–30.

Manger et al.; *Detectiuon of Sodium Channel Toxins: Directed Cytotoxicity Assays of Purified Ciguatoxins, Brevetoxins, Saxitoxins, and Seafood Extracts*; Journal of the AOAC International, vol. 78, No. 2, (1995); pp. 521–527.

Barton et al.; *Ciguatera Fish Poisoning: A Southern California Epidemic*; Western Journal of Medicine, vol. 163, (1995); pp. 31–35.

De Haro et al.; *Mass ciguatera fish poisoning after eating barracuda in Mexico: Prognostic and Therapeutic Implications*; (In French); Med Trop(Mars); vol. 57, (1997); pp. 55–58.

Nie et al.; *Probing Single Molecules and Single Nanoparticles by Surface Enhanced Raman Scattering*; science, vol. 275, (Feb. 21, 1997); pp. 1102–1106.

Hokama et al.; *Latex antibody test (LAT) for detection of marine toxins in ciguateric fish*; Journal of Natural Toxins, vol. 6, No. 1, (1997); pp. 35–50.

Bruneau et al.; *Ciguatera fish poisoning linked to the ingestion of barracuda in a Montreal restaurant*; Canada Communicable Disease Report, vol. 23–20, (Oct. 15, 1997); pp. 1–4.

Sierra–Beltran et al.; *An overview of the marine food poisoning in Mexico*; Toxicon, vol. 36, No. 11, (1998); pp. 1493–1502.

Hokama et al.; *A Simple Membrane Immunobead Assay for Detecting Ciguatoxin and Related Polyethers from Human Ciguatera Intoxication and Natural Reef Fishes*; Journal of AOAC International, vol. 81, No. 4, (1998); pp. 727–735.

Internet Search Results; Sanner et al.; *Ciguatera fish poisoning following travel to the tropics*; Lechuga–Devese et al.; *Documented case of ciguatera on the Mexican Pacific coast*; Arcila–Herrera et al.; *Ten cases of . . .* ; Blume et al.; *Ciguatera . . .* ;(Abstracts) www.ncbi.nlm.nih.gov; (PubMed) Oct. 2, 2001; 4 pages.

Hokama et al.: *A rapid enzyme–immunoassay for the detection of ciguatoxin in contaminated fish tissues*; Toxicon, vol. 21 No. 6, (1983); pp. 817–824.

Hokama et al.; *Monoclonal antibodies (Monoabs) to ciguatoxin and related polyethers*; Immunological Approaches to Coastal, Estuarine and Oceanographic Questions, Yeutsch et al., vol. 25 (1988); pp. 155–165.

Bangs, Leigh B.; *Latex Agglutination Tests*; American Clinical Laboratory News Edition; Jun. 1988, 6 pages.

McHugh et al.; *development of a micro–sphere based flourescent immunoassay and its comparison to an enzyme immunoassay for the detection of antibodies to three antigen preparations from Candida albicans*; Journal of Immunological Methods; vol. 116, (1989); pp. 213–219.

Bangs, Leigh B.; *Latex Immunoassays*; Journal of Clinical Immunoassay; vol. 23. No. 3, (1990); pp. 127–131.

Hokama, Yoshitsugi; *Recent methods for detection of seafood toxins: recent immunological methods for ciguatoxin and related polyethers*; Food Additives and Contaminants, vol. 10, No. 1, (1993); pp. 71–82.

Hokama et al.; *Human Intoxications from Hawaiian reef fishes associated with diverse marine toxins*; Journal of Natural Toxins, vol. 5, No. 2, (1996); pp. 235–246.

Bangs, Leigh B.; *New developments in particle–based immunoassays: introduction*; Pure and Applied Chemistry, vol. 68, No. 10, (1996); pp. 1873–1879.

\* cited by examiner

CIGUA-DART METHOD FOR DETECTION OF CIGUATERA TOXINS

This application claims the benefit of U.S. Provisional Application No. 60/218,048 filed Jul. 13, 2000.

BACKGROUND OF THE INVENTION

This invention relates to apparatus for collecting and concentrating analytes within a liquid medium for the purpose of identifying and quantifying the analytes using Raman, surface enhanced Raman scattering (SERS), infrared (IR) or fluorescence measurement techniques.

Ciguatoxin is the major causative toxin in ciguatera fish poisoning, a disease which remains a serious fisheries and public health problem worldwide wherever reef fish are caught and consumed. Annual worldwide estimates of people afflicted by ciguatera poisoning range from 500,000 to 1,000,000. In the United States, ciguatera is the single, leading cause of seafood poisoning. Worldwide, only 10 percent of all ciguatera cases are probably reported (Lewis, 1986). During the past five years, increased reports of ciguatera have also been documented in Mexico (Lechuga-Deveze and Sierra-Beltran, 1995; Arcila-Herrera et al., 1998; Sierra-Beltran et al., 1998), California (Barton et al., 1995), and temperate countries such as Canada (Bruneau et al., 1997; De Haro et al., 1997; Kelmme and Losch, 1997; Sanner et al., 1997; Blume et al., 1999), that import fish from ciguateric regions or whose residents travel to endemic ciguatera areas and contract the disease.

Although the ciguatera toxin-producing organism may not be considered a traditional pathogen, it does have significant global impact on human health, fisheries and their dependent economies. Ciguatera often manifests itself similar to a severe flu, causing weakness, diarrhea, muscle pain, joint aches, nausea, chills, headache, sweating and dizziness. These symptoms are often accompanied by numbness or tingling around the mouth and in the extremities, and a strange sense of temperature reversal where hot items feel cold to the touch and cold objects feel hot. Symptoms typically persist for days or weeks, but may last for months or years. Deaths are rare but can occur in severe or complicated cases.

The occurrence of ciguatera toxins in many fishes can prevent many commercially important fishes from being utilized in states or island nations with limited resources. Consequently, ciguatera can have devastating impacts on the development of small-scale commercial fisheries. In 1984, the economic losses in Florida, the Caribbean and Hawaii due to ciguatera totaled over $10 million annually. Given the rise of inflation and the continued existence of ciguatera, this figure today represents a significant loss in revenue for the fishing industries in these areas as well as those in other ciguatera affected countries. Thus, the areas that need a test method to rapidly screen fish for ciguatoxin include ciguatera endemic areas such as Hawaii, Florida, Guam, the Philippines, Japan, and the Caribbean; commercial fisheries in these areas as well as countries importing seafood from these areas; and diagnostic laboratories.

The major marine toxins associated with ciguatera poisoning have been attributed to the class of chemicals designated ciguatoxin (CTX) and its congeners. Currently, Oceanit Test Systems (OTS), a subsidiary of Oceanit Laboratories, Inc. (Oceanit), offers the only commercially available CTX detection kit, Cigua-Check®, developed by Oceanit and marketed since October 1997. Although past research has proven that CTX screening using the monoclonal antibody used in the Cigua-Check® system is effective in preventing ciguatera and can provide results within one hour, this method is designed primarily for small-scale home or field use. In order to screen potentially toxic fish from ciguatera-endemic areas, however, an even simpler, larger scale technique needs to be designed to prevent consumption of seafood tainted with CTX as well as to aid in confirming ciguatera cases caused by this toxin in the United States as well as other affected nations.

Measuring trace amounts (in parts per trillion or less) of analytes usually requires specialized techniques. Recent advances in Raman, IR and fluorescence spectroscopy have enabled increased sensitivity to detect such analytes. While methods based on identifying analytes based on their unique chemical and physical properties exist, most require considerable sample preparation and the use of expensive detectors. The need exists for techniques to measure trace amounts of analytes simply and rapidly. One example of such a trace analyte is CTX.

There is a need to prevent human illness due to ciguatera toxins by creating an innovative method to detect these harmful toxins in fish before they are incidentally ingested.

SUMMARY OF THE INVENTION

The invention measures ciguatoxin more easily and rapidly than current technologies and thus fulfills the need for a sensitive and effective method for ciguatoxin detection suitable for large-scale screening of potentially toxic fish.

The ciguatoxin molecule itself fluoresces when exposed to incident light of certain wavelengths. Why does a long hydrocarbon chain molecule such as ciguatoxin fluoresce? In Quantum Mechanics, the "Particle in a Box" scenario describes what it takes to get electronic transitions in the visible spectrum. Large organic molecules exhibit similar physics to the particle in a box. For a small molecule such as hydrogen, the transition from the ground state to the first excited electronic state occurs far in the ultraviolet. In order for the first excited state to be at a lower energy the width of the "box" or length of the molecule in this case would have to be increased. Lower energetic transitions correspond to longer wavelengths, which are observed in the fluorescence process.

The multiple side groups on long hydrocarbon chains create a de-localized electron cloud over the molecule, which have transitions that are low enough in energy to lie in the visible between the ground level and the first excited state. Isolated molecules have isolated energy levels, and larger molecules have a dense set of energy levels. For each electronic state there is a whole set of vibrational states and for each vibrational state there is a whole set of rotational states.

In a liquid, the molecules are free to move around, but for larger molecules, as soon as they move by even a fraction of their diameter they collide with a neighboring molecule. These collisions will cause decay from excited states to lower excited states or to the ground state. This collisional decay process broadens the absorption spectrum substantially. The isolated discrete electronic, vibrational, rotation levels broaden and overlap into what looks like a continuum of levels resulting in a band of energy levels.

In thermal equilibrium the population of electrons in the energy levels follow the Maxwell Boltzmann distribution. The range of energies is so broad that the molecules are all near the bottom of the ground state within each energy band. Transitions occur from anywhere in the band of ground levels to anywhere in the first excited state.

An example of this phenomenon can be seen with rhodamine 6G "Texas Red," a reddish-orange colored dye used in dye lasers and as a "fluorescent beacon" in laser scanning confocal microscopy. Single molecules of rhodamine 6G have also been detected using SERS. If a molecule such as this absorbs energy it is raised into the first excited state, and will be in a high lying vibration rotation state well above the bottom of the first excited state. This excess energy is lost very rapidly due to collisions with the neighboring molecules in the liquid, lowering the energy to the bottom of the band of first excited states. Optical transitions can occur from the bottom of the first excited state to anywhere in the band of ground states. This mechanism establishes a natural population inversion, and the sample of dye will have strong fluorescence when illuminated with light. This occurrence may also explain why the ciguatoxin molecule fluoresces.

The invention has many advantages over present ciguatoxin detection techniques. First, it requires far less time to analyze unknown samples, in the range of minutes as opposed to hours. Second, because the invention is easy to use and the spectra automatically compared to known samples, it will be simple to use. Third, because of these two factors, the invention can be easily adapted for laboratory use to analyze clinically implicated fish as well as for commercial use to screen fish species associated with ciguatera.

The invention is a novel, rapid quantitative detection system to measure ciguatera fish poisoning toxins in fish on a commercial scale. It may also be used to verify the presence of ciguatoxin in humans suspected of having ciguatera and thus aid in diagnosis and treatment of the disease.

Briefly, the invention consists of a hollow reaction chamber with hollow tubes on either end. On one end an open-ended "fish coring tube," is used to collect the fish sample. By pushing the coring tube forcibly into a fish, a small cylinder of flesh (or core) is trapped inside the tube. On the other end a closed-ended glass "assay tube," is used for analysis of the extracted sample.

A reagent cap containing solvent in a squeezable bag is screwed onto the fish coring tube, thereby pushing the fish sample into the main chamber. Squeezing the reagent cap causes a thin membrane to rupture allowing the reagent contents to enter the reaction chamber. For SERS spectroscopy, a second reagent cap containing silver colloid with antibody solution may be used to introduce the second solution into the chamber. The chamber is then placed upright to allow the solution in the chamber to filter into the assay tube for analysis. This device is easy to use and requires a minimum effort by the user.

Raman scattering processes yield much less intense signals than fluorescence processes. They are, however, much more specific and can be used to identify particular chemicals. For these reasons, fluorescence spectroscopy may be effectively used to screen large quantities of fish for ciguatoxins, while SERS may be used to confirm the presence of as well as to quantify ciguatoxins in suspect fish.

Importantly, these techniques may be applied to detect other toxins as well as a multitude of other compounds presently non-measurable due to detection limits of existing techniques. The invention can be easily adapted to detect other toxins often present in seafood. The ability to quickly and cheaply test large quantities of fish is a prime requirement to assure the wholesomeness of fish destined for human consumption.

The invention allows rapid examination of numerous fish in an assembly-line fashion by laboratory technical personnel. The lower cost per test and much higher through-put rate are huge advantages in commercial fish markets, which presently lack any such screening methods.

This method may be adapted to measure countless other compounds of interest, providing only that an antibody has been made against them. The invention provides a new approach to the concept of using Raman spectroscopy to detect and quantify immunological assay results. Furthermore, unlike the few previously developed systems, the invention is designed for rapid use in the laboratory, field, or industrial settings.

The new method incorporates immunological and Raman technologies, enabling rapid, quantitative detection of ciguatera toxins suitable for large-scale testing. The method may be used by clinical laboratories to aid in the diagnosis of ciguatera cases and hence, to improve treatment for this disease. In addition, the method may also be used by commercial fisheries for large-scale screening of suspected fish species collected from endemic ciguatera areas.

The device "Cigua-Dart" is created for incorporation into a large-scale commercial screening process for ciguatera toxins in fish, using fluorescence spectroscopy, Surface-Enhanced Raman Spectroscopy (SERS), or both. The first method is based on the fluorescence signal from ciguatoxin exposed to a certain wavelength. The second method incorporates immunological and Raman spectroscopy technologies.

Using fluorescence spectroscopy the "Cigua-Dart" device serves as both the tissue collection apparatus and reaction chamber. A preferred embodiment of the dart is made up of three pieces of molded plastic or glass, one central body and two end caps. However, the number of pieces is not limited to three. Preferably, the body consists of a main chamber about 30 mm long and 10 mm in diameter. In a preferred embodiment, a thinner tube approximately 16 mm long and 4 mm in diameter extends from each end of this chamber. One of these tubes, the "assay tube", is either glass or plastic and sealed at the end; the other, the "fish coring tube", is open-ended. Preferably, two end caps fit over these tubes. One of the preferred end caps is a simple sliding fit device that prevents damage to the sealed assay tube and allows ease of handling. The second preferred end cap is a more complicated design consisting of a hollow fluid delivery tube and liquid test reagent in a soft, squeezable, initially sealed bulb. This end cap may be screwed onto the fish coring tube.

In a preferred embodiment, the steps to perform a test for Ciguatoxin are:

a. The reagent cap is unscrewed from the main body exposing the open-ended fish coring tube. This is pressed into the fish so that a core of tissue is excised and trapped within it. The end of the tube may be beveled to facilitate insertion.

b. The reagent cap is screwed back onto the main chamber. The hollow fluid delivery tube is then positioned so as to slide into the fish coring tube and push the tissue sample into the main chamber of the dart.

c. The soft bulb on the reagent cap is pressed, pressurizing the liquid intake and breaking a seal so that a measured quantity of solvent, such as but not limited to methanol-d4, flows up the delivery tube, into the main chamber, and into contact with the fish tissue.

d. The dart is first shaken to mix the contents and then left lying with the long dimension horizontal for a period of time so that the solvent can leach the toxin from the tissue.

e. The dart is stood vertically on a flat surface so that the solvent percolates through the glass wool or other type of filtering media to filter out large particles of tissue, and down into the sealed assay tube.

f. The protective cap is removed exposing the thin-walled assay tube. Spectroscopic analysis is then performed on the contents of the exposed assay tube.

The only difference for Raman spectral analysis is the addition of a third end cap. This end cap is identical to the one described for the "fish coring tube" end of the Cigua-Dart device, except that instead of a solvent, such as methanol-d4, it contains MAb-CTX in a silver colloid suspension as a reagent.

In a preferred embodiment, the steps to perform a Raman spectral analysis are:

a. The reagent cap is unscrewed from the main body exposing the open-ended fish coring tube. This is pressed into the fish so that a core of tissue is excised and trapped within it. The end of the tube may be beveled to facilitate insertion.

b. The reagent cap is screwed back onto the main chamber. The hollow fluid delivery tube is then positioned so that it slides into the fish coring tube and pushes the tissue sample into the main chamber of the dart.

c. The soft bulb on the reagent cap is pressed, pressurizing the liquid inside and breaking a seal so that a measured quantity of solvent, such as but not limited to methanol-d4, flows up the delivery tube, into the main chamber, and into contact with the fish tissue.

d. The dart is first shaken to mix the contents and then left lying with the long dimension horizontal for a period of time.

e. With the dart held with the fish coring end upright, the first reagent cap is removed and replaced with a second reagent cap, this one containing the MAb-CTX in silver colloid suspension as a reagent. The dart is shaken to mix the contents and is then left lying horizontally for a period of time.

f. The dart is stood vertically on a flat surface so that the solvent percolates through the glass wool or other type of filtering media to filter out large particles of tissue, and down into the sealed assay tube.

g. The protective cap is removed exposing the thin-walled assay tube. Spectroscopic analysis may then be performed on the contents of the exposed assay tube.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
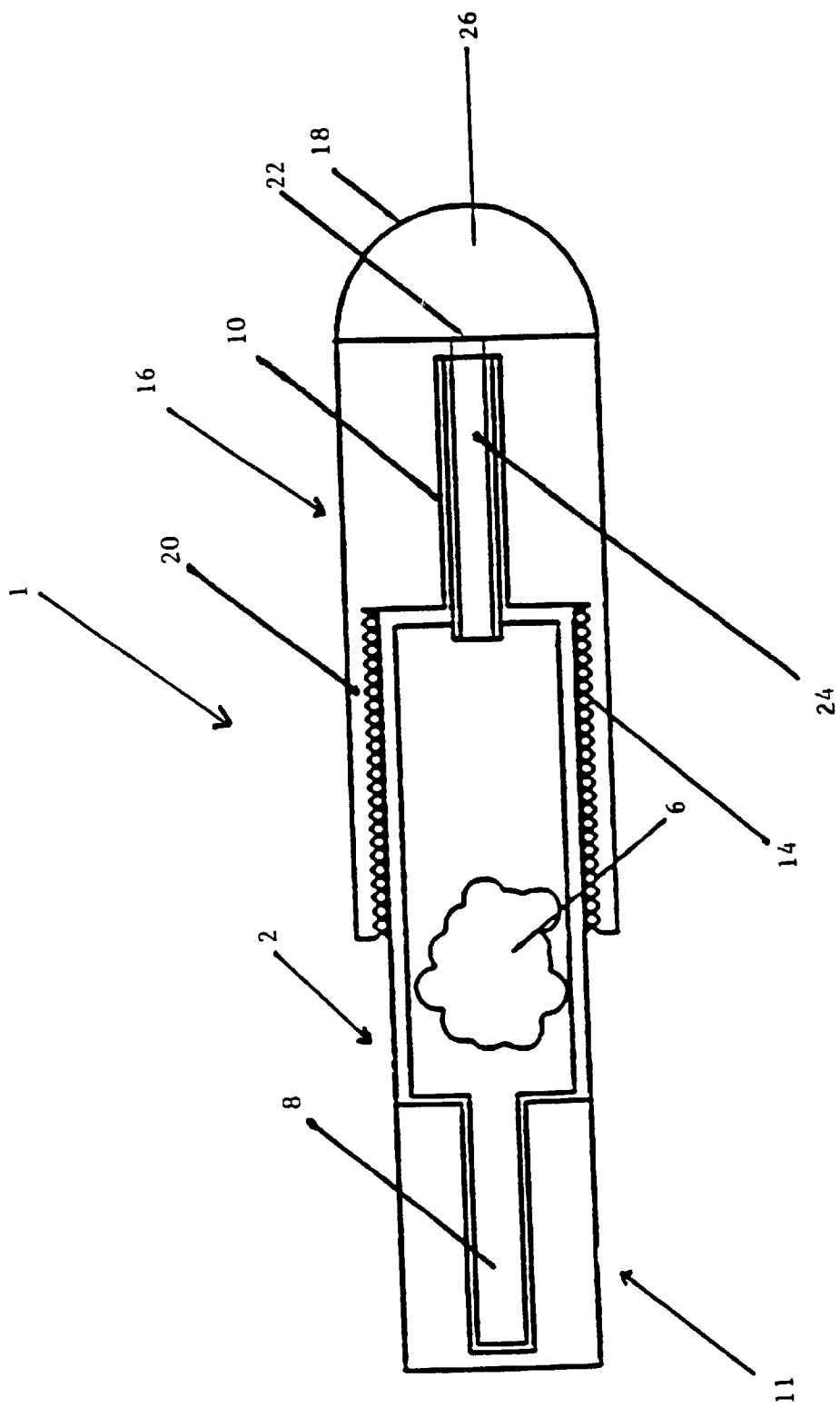
FIG. 1 is a cross-section of a Cigua-Dart showing the end caps attached to the reaction chamber.

In a preferred embodiment, the Cigua-Dart 1 is made up of preferably, but not limited to, three pieces of molded plastic or glass, one central body 2 and end caps 11, 16. As seen in FIGS. 1 and 2B, the preferred central body 2 comprises a main chamber preferably about 30 mm long and 10 mm in diameter. From each end of this chamber extends a thinner tube 8, 10. Preferably, the tubes are approximately 16 mm long and 4 mm in diameter. One of these tubes, the assay tube 8, is sealed at one end; the other tube, the fish coring tube 10, has open ends. Preferably, an open end of the fish coring tube 10 away from the central body 2 is beveled 12 to facilitate removing tissue from a fish to be tested. End caps 11, 16 fit over these tubes.

Figure 2A:
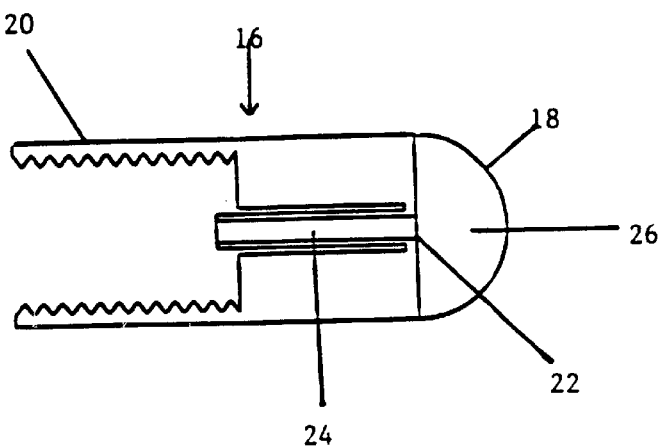
FIG. 2A is a cross-sectional view of a reservoir end cap of the Cigua-Dart.
Figure 2B:
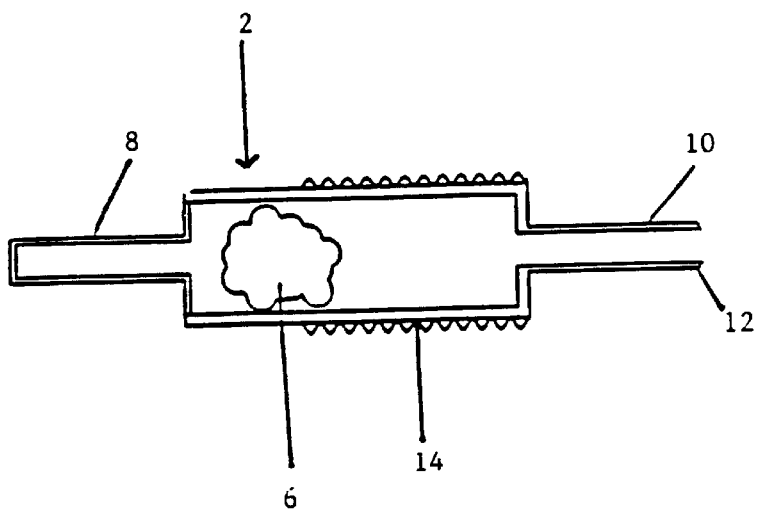
FIG. 2B is a cross sectional view of the central body of the Cigua-Dart.
Figure 2C:
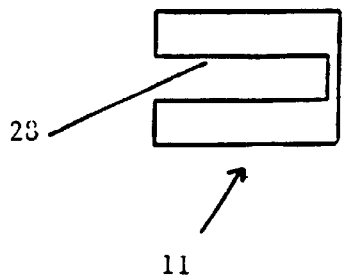
FIG. 2C is a cross-sectional view of an end cap for the assay tube of the Cigua-Dart.

FIGS. 2A–2C are cross-sectional views of the of the preferred components of a one-chambered collection/reaction chamber apparatus. FIG. 2A is a protective cap that covers the detection end of the reaction chamber. FIG. 2B is the reaction chamber. One end of the chamber is open, forming the sample coring tube. The end of the fish coring tube is beveled to facilitate sample collection. The other end of the chamber is closed, forming the detection tube. The part of the reaction chamber closest to the fish coring tube may be threaded so the reagent cap can be screwed onto the chamber during sample analysis. FIG. 2C is the reagent cap. The inner surface of the cap may be threaded to fit onto the corresponding threaded portion of the reaction chamber. In the top of the cap is a hollow chamber which contains the reagent(s). This chamber is connected to an open-ended hollow tube which fits into the fish coring tube when the reagent cap is screwed onto the reaction chamber. Prior to commencement of the assay procedure the hollow reagent chamber is separated from the hollow tube by a thin membrane.

FIGS. 2A and 2C show preferred end caps. End cap 11 may be a simple sliding fit device that prevents damage to the sealed assay tube 8 and allows ease of handling. End cap 16 comprises a hollow fluid delivery tube 24 and a liquid reagent 26 in a soft, squeezable bulb 18, which is initially sealed 22. Preferably, end cap 16 is screwed onto the fish coring tube 10 via grooved extensions 20 on the end cap 16 which correspond with external grooves 14 on the central body 2. However, the means for connecting the end cap with the main body of the device may be varied.

EXAMPLE 1

The first technique is simple fluorescence spectroscopy to detect ciguatoxins. The invention is used to collect samples of previously determined as ciguatoxic and non-ciguatoxic using published methods. Cigua-Darts are made up of multiple pieces of molded plastic or glass, one central body and two end caps. The body preferably consists of a main chamber about 30 mm long and 10 mm in diameter. From each end of this chamber extends a thinner tube approximately 16 mm long and 4 mm in diameter. One of these tubes ("Assay tube") is either glass or plastic and sealed at the end; the other ("Fish coring tube") is open. Two end caps fit over these tubes. One of the end caps may be a simple sliding fit device that prevents damage to the sealed Assay tube and allows ease of handling. The second end cap may be of a different design consisting of a hollow fluid delivery tube and liquid test reagent in a soft, squeezable, initially sealed bulb. This end cap may be screwed on to the fish coring tube.

The preferred steps of a test for ciguatoxins are:

a. A reagent cap 16 is unscrewed from the main body 2 exposing the open-ended fish coring tube 10. This is pressed into the fish so that a core of tissue is excised and trapped within it. The end of the tube 10 may be beveled 12 to facilitate insertion.

b. The reagent cap 16 is screwed back onto the main chamber 2. The hollow fluid delivery tube 24 is then positioned so that it slides into the fish coring tube 10 and pushes the tissue sample into the main chamber 2 of the dart.

c. The soft bulb 18 on the reagent cap 16 is pressed, pressurizing the liquid intake and breaking seal 22 so that a measured quantity of solvent 26, such as but not limited to methanol-d4, flows up the delivery tube 24, into the main chamber 2, and into contact with the fish tissue.

d. The dart 1 is first shaken to mix the contents and is then left lying with the long dimension horizontal for a period as L of time so that the solvent 26 can leach toxin from the tissue.

e. The dart 1 is stood vertically on a flat surface so that the solvent 26 can percolate through a filtering medium such as glass wool 6, filtering out large particles of tissue, and down into the sealed assay tube 8.

f. The protective cap 11 is removed exposing the thin-walled assay tube 8. Spectroscopic analysis can then be performed on the contents of the exposed assay tube 8.

The steps to perform a test for ciguatoxins are not, however, limited to the above preferred steps.

The basic elements of a detection system for fluorescence spectral analysis for ciguatoxin preferably include a laser power blue line to illuminate the samples, a spectrometer, a CCD (charged coupled device) detector, which may be attached to a simple electronic device that triggers a visible or audible signal if toxic fish tissue is detected.

In a preferred embodiment, an approximately 30 mW laser power blue line at 488 nm, a SPEX 0.34 m spectrometer and a thermoelectrically cooled ICD are used.

Fluorescence spectroscopy is used effectively to screen large quantities of fish for ciguatoxins, while Raman spectral analysis and SERS is used to confirm the presence of, as well as to quantify, ciguatoxins in suspect fish. Both techniques may be applied to detect toxins and compounds other than ciguatoxins.

The only difference for a Raman spectral analysis is the addition of a third end cap 16. This end cap 16 is identical to the one described for the "fish coring tube" end of the device 16, except that instead of methanol-d4 reagent 26, it contains MAb-CTX in a silver colloid suspension as a reagent 26.

EXAMPLE 2

The second technique employs immunological and SERS spectroscopy for more specific and sensitive analysis of ciguatoxin.

The assay procedure is similar to that described above in Example 1, with the exception that an extra reagent cap is added. The first reagent cap contains a solvent. The second reagent cap contains a silver colloid suspension and a predetermined concentration of antibody specific for the analyte added.

The only difference for Raman spectral analysis is the addition of a third end cap. This end cap may be identical to the one described for the "Fish coring tube" end of the device, except that instead of solvent it contains antibody specific for the analyte in a silver colloid suspension.

The basic elements needed for a scattered light detection system may include: a Raman spectrometer, confocal microscope, a laser diode, holographic filter, CCD detector, and analytical software in a miniaturized computer system.

The preferred steps to perform a Raman spectral analysis test for ciguatoxins are:

a. The reagent cap 16 is unscrewed from the main body 2 exposing the open-ended fish coring tube 10. This is pressed into the fish so that a core of tissue is excised and trapped within it. The end of the tube 10 may be beveled 12 to facilitate insertion into fish tissue.

b. The reagent cap 16 is screwed back onto the main chamber 2. The hollow fluid delivery tube 24 is then positioned so that it slides into the fish coring tube and pushes the tissue sample into the main chamber 2 of the dart.

c. The soft bulb 18 on the reagent cap 16 is pressed, pressurizing the liquid inside and breaking seal 22 so that a measured quantity of solvent 26, such as but not limited to methanol-d4, flows up the delivery tube 24, into the main chamber 2, and into contact with the fish tissue.

d. The dart 1 is first shaken to mix the contents and then left lying with the long dimension horizontal for a period of time.

e. With the dart 1 held with the fish coring end 10 upright, the first reagent cap 16 is removed and replaced with a second reagent cap 16, this one containing MAb-CTX in silver colloid suspension as a reagent 26. The dart 1 is first shaken to mix the contents and is then left lying horizontally for a period of time.

f. The dart is stood vertically on a flat surface so that the solvent 26 percolates through a filtering medium such as glass wool 6, which filters out large particles of tissue, and down into the sealed assay tube 8.

g. The protective cap 11 is removed exposing the thin-walled assay tube 8. Spectroscopic analysis may then be performed on the contents of the exposed assay tube 8.

The steps to perform a Raman spectral analysis are not, however, limited to the above preferred steps.

In a preferred method, the silver colloids are prepared by adding 6 mL of 34 mM sodium citrate dropwise over a one-hour period via buret to 1 L of rapidly boiling and stirred 0.3 mM silver nitrate. After the solution is boiled for an additional hour and cooled to room temperature the volume is adjusted. Preferably, the silver colloids are filtered through a glass fiber filter prior to use. In a preferred method, the colloids are fractionated by sedimentation in a graduated cylinder at room temperature over a 10-day period. Successive aliquots are carefully drawn off and stored in separate light-protective containers kept in the dark until ready for use. Immediately prior to use the colloids are activated with 0.585 g sodium chloride per L. The silver colloids may be prepared using methods other than the preferred method.

Preferably, MAb-CTX is prepared at concentrations ranging from 10 to 100 ng per ml of phosphate buffered saline (PBS). The basic preferred elements for a ciguatoxin detection system for Raman spectral analysis include a Raman spectrometer, a confocal microscope, and an argon laser, a Krypton laser, a holographic filter, a CCD (charged coupled device), and analytical software in a computer system. Spectra of samples are measured from 500 to 700 nm.

A preferred embodiment of a detection system for Raman spectral analysis comprises a SPEX Triple Raman spectrometer, an E. Leitz optical microscope, a Spectra Physics 2000 Argon laser, a Spectra Physics Series 2020 Krypton laser for illuminating samples with 457.9 nm radiation, a CCD (charged coupled device) camera cooled with liquid nitrogen to −70° C. and a miniaturized computer system. The detection system for Raman spectral analysis is not limited to the preferred embodiment.

One limitation of using conventional Raman spectroscopy is its low sensitivity, often requiring the use of powerful and costly laser sources for excitation. The sensitivity of the Raman technique can be enhanced in several ways. The first preferred method of enhancement is to use surface-enhanced Raman spectroscopy, or SERS. In SERS, substrates are used to magnify the Raman signal. Typical substrates include electrodes, island films or colloidal sols. The use of this technique increases up to $10^8$ times the conventional Raman scattering efficiency.

The second preferred method of enhancement is to employ the use of antibodies in the SERS technique. Raman spectroscopy has already been used to distinguish between bound and unbound antibodies in test solutions. A known concentration of antibody added to a solution will emit a characteristic Raman spectrum. Antigen added to this solution will complex with the available antibody, thereby changing the Raman spectrum. The degree of change will be proportional to the concentration of antigen and antibody. A similar technique, surface-enhanced resonance Raman scattering (SERRS) has been used to yield a linear relationship between the intensity of SERRS signals and antigen concentration over a given range. Other methods of enhancing the sensitivity of the Raman technique may be used.

While the invention has been described with reference to specific embodiments, modifications and variations of the invention may be constructed without departing from the scope of the invention, which is described in the following claims.

We claim:

1. Toxin detection apparatus comprising a housing having a main chamber for receiving a tissue sample, first and second end chambers having areas smaller than an area of the main chamber and communicating with opposite ends of the main chamber, a removable reagent cap for coupling with the first end chamber, a reagent in the reagent cap for expressing on the tissue sample in the chambers, an assay in the second end chamber for assaying substances leached from the tissue sample, and an analyzer for receiving data from the assay and analyzing substances in the tissue sample for detecting toxins.

2. The apparatus of claim 1, wherein the first end chamber comprise an open-ended tissue coring tube for collecting tissue sample.

3. The apparatus of claim 2, wherein the second end chamber comprise a closed-ended assay tube forming the assay for analyzing the tissue sample.

4. The apparatus of claim 3, wherein the reagent cap comprises first and second squeezable reagent caps interchangeably coupled to the coring tube for pushing the tissue sample and the first and second reagents respectively into the main chamber.

5. The apparatus of claim 4, wherein the first reagent in the first reagent cap comprises a solvent and the second reagent in the second reagent cap comprises a suspension comprising silver colloid particles and antibody specific for analytes of interest in the tissue sample.

6. The apparatus of claim 5, further comprising a solution formed by the reagent and the analytes and a filter for filtering the solution into the assay tube for analysis.

7. The apparatus of claim 6, wherein the filter comprises a filtration medium.

8. The apparatus of claim 6, further comprising a protective cap for covering the second end chamber.

9. Toxin detection apparatus comprising a main chamber for receiving a tissue sample, first and second end chambers on opposite ends of the main chamber, a removable reagent cap for coupling with the first end chamber, a reagent in the reagent cap for expressing on the tissue sample in the chambers, an assay in the second end chamber for assaying substances leached from the tissue sample, a detector for receiving data from the assay, analyzing and detecting toxins, and the first end chamber forming an open-ended tissue coring tube, wherein the tissue coring tube is beveled to facilitate sample collection.

10. The apparatus of claim 1, further comprising connectors on the first end chamber and fasteners on the reagent cap for removably connecting the reagent cap to the first end chamber.

11. The apparatus of claim 10, wherein the connectors and fasteners are threads.

12. The apparatus of claim 4, wherein each reagent cap comprises a hollow chamber for containing the reagents, and an open-ended hollow tube connecting the hollow chamber and the main chamber through the coring tube when the reagent cap is coupled to the first end chamber, wherein the first or the second squeezable reagent cap expresses the reagent from the hollow chamber into the main chamber on squeezing.

13. The apparatus of claim 12, further comprising a thin rupturable membrane between the hollow chamber and the hollow tube for rupturing and expressing the reagents.

14. Toxin detection apparatus comprising a main chamber for receiving a tissue sample, first and second end chambers on opposite ends of the main chamber, a removable reagent cap for coupling with the first end chamber, a reagent in the reagent cap for expressing on the tissue sample in the chambers, an assay in the second end chamber for assaying substances leached from the tissue sample, a detector for receiving data from the assay, analyzing and detecting toxins, and wherein the first end chamber comprises an open-ended tissue coring tube for collecting tissue sample, wherein the tissue coring tube further comprises bevelled tips.

15. The apparatus of claim 3, further comprising an energy source for supplying optical energy to the assay and wherein the analyzer is a detector for detecting optical energy from the assay.

16. The apparatus of claim 15, wherein the optical energy comprises radiation of varying wavelengths and intensities, and wherein the assay tube reflects, shifts or scatters the optical energy for detecting with the detector.

17. The apparatus of claim 16, wherein the detector comprises a charge-coupled device.

18. The apparatus of claim 16, further comprising a computing device for analyzing data collected by the detector, comparing analyzed data with data of control samples, quantifying and outputting analysis results corresponding to detected toxins.

19. The apparatus of claim 1, wherein the tissue sample is a seafood tissue sample.

20. The apparatus of claim 1, wherein the tissue sample is a fish tissue sample.

* * * * *